United States Patent [19]
Boie et al.

[11] 4,133,958
[45] Jan. 9, 1979

[54] 2-EQUIVALENT YELLOW COUPLERS

[75] Inventors: Immo Boie, Odenthal; Karl Küffner, Unterhaching; Gertrud Kirchhoff, Leverkusen; Karl-Wilhelm Schranz, Langenfeld, all of Germany

[73] Assignee: AGFA-Gevaert Aktiengesellschaft, Fed. Rep. of Germany

[21] Appl. No.: 794,358

[22] Filed: May 6, 1977

Related U.S. Application Data

[63] Continuation-in-part of Ser. No. 606,423, Aug. 21, 1975, abandoned.

[30] Foreign Application Priority Data

Aug. 31, 1974 [DE] Fed. Rep. of Germany ....... 2441779

[51] Int. Cl.² ........................................... C07D 233/70
[52] U.S. Cl. .................................... 548/321; 96/56.5; 96/100 N; 544/139; 548/305; 548/318
[58] Field of Search ....................... 548/305, 321, 318; 544/139

[56] References Cited
U.S. PATENT DOCUMENTS

| 3,265,506 | 8/1966 | Weissberger et al. | 260/556 B |
| 4,026,706 | 5/1977 | Nakamura et al. | 96/74 |

FOREIGN PATENT DOCUMENTS 2329587  1/1975 Fed. Rep. of Germany.

OTHER PUBLICATIONS

Neblette, Photography, Its Materials and Processes, D. Van Nostrand Co., New York (1962) p. 241-246.

Primary Examiner—Richard Raymond
Attorney, Agent, or Firm—Connolly and Hutz

[57] ABSTRACT

Desirable 2-equivalent yellow-forming couplers in which a 1,3-diazolone-2-ring as splittable group is attached by the nitrogen in its 1-position to the coupling position of the 2-equivalent yellow-forming coupler and in which the diazolone ring has a C=C double bond adjacent to the nitrogen atom in its 1-position, have improved photographic properties in particular with respect to improved reactivity on chromogenic development and improved stability of the couplers as well as the dyes produced from them on chromogenic development in a photographic material which has been subjected to storage under moist and/or warm conditions.

5 Claims, No Drawings

2-EQUIVALENT YELLOW COUPLERS

This application is a continuation-in-part of application Ser. No. 606,423 filed Aug. 21, 1975, and subsequently abandoned.

The present invention relates to new 2-equivalent yellow-forming couplers suitable for use in color photographic materials.

It is known to produce colored photographic images by developing the exposed silver halide in a light-sensitive silver halide emulsion layer with an aromatic developer substance which contains primary amino groups, in the presence of a color coupler. The color coupler reacts with the oxidized color developer to form an image dye which corresponds to the silver image.

Simple couplers for producing the yellow image dye contain a methylene group which is activated by two attached carbonyl groups and which react with the oxidized color developer during the process of color development to form a yellow dye. This reaction requires four equivalents of developable silver halide to produce one mol of yellow dye and these couplers are therefore known as 4-equivalent couplers. Other couplers are known which contain an activated methylene group in which one hydrogen has been substituted by a group which can be split off during the coupling reaction. In this case only two equivalents of developable silver halide are required to form the dye. These couplers are therefore known as 2-equivalent couplers.

Inasmuch as the quantity of silver halide required to form a given quantity of dye with a 2-equivalent coupler is about half the quantity required in the case of a 4-equivalent coupler, a smaller quantity of silver halide may be used for preparing the light-sensitive recording material. A thinner emulsion layer may therefore be used, and this in turn has an advantageous effect on the resolution capacity of the photographic material and sharpness of the image.

Among the 2-equivalent yellow-forming couplers known in the art, those which contain chlorine as splittable substituent have proved in practice to be sufficiently rapid to ensure satisfactory color densities even when very short processing methods are employed. However, 2-equivalent yellow-forming couplers which contain splittable chlorine frequently have a deleterious effect on the photographic properties of the silver halide emulsion. As described in British Patent Specification No. 1,351,395, only certin yellow-forming couplers based on benzoylacetanilide and containing splittable chlorine are photographically sufficiently inert to cause an acceptable low level of color fogging during development. However, they are generally not satisfactory with respect to the photographic requirement that the unprocessed photographic material containing the coupler withstand storage under moist, warm conditions without significantly increased fogging.

It is one of the objects of the present invention to provide new 2-equivalent yellow-forming couplers which are easily prepared and the reactivity of which in color photographic development processes is sufficiently high, at least comparable to that of 2-equivalent couplers containing splittable chlorine, and which do not deleteriously affect the photographic properties of the color photographic materials.

It has now been found that improved 2-equivalent yellow-forming couplers have an open-chain ketomethylene structure in which one of the hydrogen atoms of the activated methylene group has been substituted by the 1-nitrogen atom of a 1,3-diazolone-2 group which has a carbon to carbon double band between positions 4 and 5.

The 2-equivalent yellow-forming couplers according to this invention particularly correspond to the following general formula:

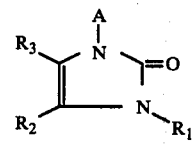

in which $R_1$ represents hydrogen; an alkyl group, preferably containing 1 to 4 carbon atoms, e.g. methyl, ethyl or t-butyl; or an alkoxy carbonyl group in which the alkoxy group contains from 1 to 5 carbon atoms, such as ethoxy carbonyl;

$R_2$ and $R_3$ represent either the same or different substituents selected from the group consisting of hydrogen, alkyl and alkoxycarbonyl in which the alkoxy group contains from 1 to 5 carbon atoms, such as butoxycarbonyl, propoxycarbonyl or methoxycarbonyl, but at least one of $R_2$ and $R_3$ represents an alkoxy carbonyl group, or $R_2$ and $R_3$ together represent the atoms required to complete a condensed benzene ring, which ring is further substituted with two chlorine atoms to form the 5,6-dichlorobenzimidazolone group;

A represents a radical of a yellow-forming coupler having an open-chain keto-methylene structure in which a methylene group is activated by two attached carbonyl groups, or by one carbonyl and one cyano group and the radical being obtained by removing a hydrogen atom from the activated methylene group.

A may be represented by the following formula (I):

where

B represents an alkyl radical having 1 – 32 C-atoms, preferably 1 – 18 C-atoms, branched or unbranched; in the case of a secondary or tertiary alkyl radical the secondary or tertiary carbon atom should preferably be linked directly with the carbonyl group; or an alkoxyalkyl radical, a bicycloalkyl radical, a heterocyclic radical or an aryl radical, especially a phenyl radical which may, if necessary, be substituted once or several times by alkyl having 1 – 18 C-atoms, aryl, aralkyl, alkoxy having 1 – 18 C-atoms, aroxy, halogen (e.g. fluorine or bromine), acyl, acyloxy, acylamino, amino-, carbamyl- or sulfamyl groups which may be substituted by identical or different aryl, aralkyl, alkyl or heterocyclic radicals, sulfo or carboxy;

B' represents cyano or the group

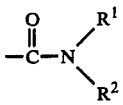

$R^1$ represents hydrogen or a short-chain alkyl group having 1 – 5 C-atoms, for example methyl or ethyl and $R^2$ represents an alkyl group having 1 – 18 C-atoms or preferably an aryl group, for example a phenyl group which may be substituted by identical or different groups such as alkyl having 1 – 18 C-atoms, aryl, aralkyl, alkoxy, aroxy, halogen (e.g. fluorine or bromine), acyl, acyloxy, acylamino, amino, carbamyl or sulfamyl groups which may be substituted by identical or different aryl, aralkyl, alkyl or heterocyclic radicals, sulfo or carboxy.

Preferred coupler radicals are those which are derived from 4-equivalent yellow couplers that produce dyes having the desired absorption and stability required in practice. Benzoylacetanilides in particular alkoxybenzoylacetanilides and pivaloyl acetanilides which may be substituted in the anilide group of the coupler molecule by one or several, optionally one to three, substituents preferably in the 2-, 4- and 5-position of the anilide group, are shown to be of preferred practical importance.

For further information on the wide range of structures suitable for the yellow coupler backbones as shown in the above formula I, reference may be made to the Loria U.S. Pat. No. 3,644,498 and particularly to the formula in column 2 thereof in which the R shown corresponds to B in formula I above and in which $R^1$ corresponds to B' in formula I above.

When $R_1$ represents hydrogen, the heterocyclic group of the above formula which is split off may, of course, also exist in tautomeric forms as follows:

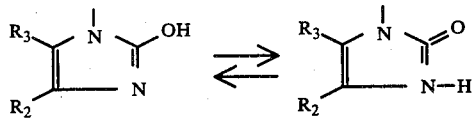

The new yellow-forming couplers according to the invention have a high coupling activity, that is to say they give rise to dye images with a high color density, and they are particularly suitable for use in light-sensitive silver halide emulsion layers of color photographic single- or multilayer materials.

The new yellow-forming couplers are also advantageously distinguished over prior art compounds by having a highly diminished basic fog, in particular when pivaloyl acetanilide couplers are used. The stability of the color couplers under the condition of storage in a heating cupboard is also further improved.

The following are examples of suitable yellow-forming couplers according to the invention:

Table 1

Structure: t-butyl—C(=O)—CH(X)—CONH—[phenyl with R4 (ortho) and R5 (para)]

| No. | X | R4 | R5 | Mp (°C) |
|---|---|---|---|---|
| 1 | hydantoinyl-COOCH3 | Cl | —NH—CO(CH2)3—O—(2-t-C5H11, 4-t-C5H11-phenyl) | 170–172 |
| 2 | hydantoinyl-COOC2H5 | OC16H33 | SO2NHCH3 | 115–118 |
| 3 | hydantoinyl-COOCH3 | OC16H33 | —NH—CO(CH2)3—O—SO2N(CH3)2 | 105 |
| 4 | hydantoinyl-COOC4H9(n) | OC16H33 | H | 132–133 |
| 5 | hydantoinyl-COOCH3 | Cl | —NH—CO—CH2—O—(4-Cl, 2-C14H29-phenyl) | 98–101 |
| 6 | hydantoinyl-COOC4H9(iso) | Cl | —NH—CO(CH2)3—O—(2-t-C5H11, 4-t-C5H11-phenyl) | oily |

Table 1-continued

| No. | X | R₄ | R₅ | Mp (°C) |
|---|---|---|---|---|
| 7 | pyrrolidinone-COO(CH₂)₂CH(CH₃)CH₃ | OC₁₆H₃₃ | H | 120 – 121 |
| 8 | pyrrolidinone-COOCH₃ | OC₁₆H₃₃ | SO₂NHCH₃ | 96 – 98 |
| 9 | pyrrolidinone-COOC₄H₉(iso) | OC₁₆H₃₃ | SO₂NHCH₃ | 101 – 103 |
| 10 | pyrrolidinone-COOC₄H₉(iso) | OC₁₄H₂₉ | Cl | 119 – 120 |
| 11 | pyrrolidinone-COOC₄H₉(iso) | OC₁₆H₃₃ | CH₃ | 91 – 93 |
| 12 | pyrrolidinone-COOCH₃ | OC₁₆H₃₃ | Cl | 102 – 104 |
| 13 | pyrrolidinone-COOCH₃ | OC₁₆H₃₃ | H | 120 |

Table 1-continued t-butyl—C(=O)—CH(X)—CONH—[phenyl with R$_4$, R$_5$]

| No. | X | R$_4$ | R$_5$ | Mp (°C) |
|---|---|---|---|---|
| 14 | -N(COC$_2$H$_5$)-(3,4-dichlorophenyl) | OC$_{16}$H$_{33}$ | SO$_2$NHCH$_3$ | 80 |
| 15 | -N(COC$_2$H$_5$)-(3,4-dichlorophenyl) | OC$_{14}$H$_{29}$ | H | 114 |
| 16 | hydantoin-N-yl with COOCH$_3$ | Cl | NH—CO—O—CH(C$_2$H$_5$)—O—[2,4-di-t-C$_5$H$_{11}$-phenyl] | 110–115 |
| 17 | hydantoin-N-yl with COOCH$_3$ | Cl | NH—CO—O—CH(CH$_3$)—CH$_2$—O—[2-cyclopentyl-5-t-C$_4$H$_9$-phenyl] | 136–144 |
| 18 | hydantoin-N-yl with COOCH$_3$ | —N(CH$_3$)(C$_{18}$H$_{37}$) | —SO$_3$H | 255–258 |

Table 1-continued $$\text{t-butyl}-\overset{O}{\overset{\|}{C}}-\overset{}{\underset{X}{C}}H-CONH-\underset{R_5}{\overset{R_4}{\bigcirc}}$$

| No. | X | $R_4$ | $R_5$ | Mp (°C) |
|---|---|---|---|---|
| 19 | (imidazolidinone-COOCH₃) | —OCH₃ | NH—CO—O—CH(CH₂CH₃)— attached to phenyl with C₄H₉(t) | 158 – 162 |
| 20 | (imidazolidinone-COOCH₃) | —OCH₃ | NH—CO—(CH₂)₃—O— attached to phenyl with C₅H₁₁(t), C₅H₁₁(t) | 186 – 189 |
| 21 | (imidazolidinone-COOCH₃, CH₃) | OC₁₆H₃₃ | SO₂—NH—CH₃ | 123 – 125 |
| 22 | (imidazolidinone-COOCH₃) | OCH₃ | NH—SO₂—C₁₆H₃₃ | 74 |
| 23 | (imidazolidinone-COOCH₃) | morpholino | SO₂—NH—C₁₈H₃₇ | oily |
| 24 | (imidazolidinone-COOCH₃) | CH₃-C(CH₃)₂-CH₂-C(CH₃)₂-phenyl-O— | SO₂N(CH₃)(C₁₈H₃₇) | 132 – 135 |

Table 1-continued t-butyl—C(=O)—CH(X)—CONH—[phenyl with R₄, R₅]

| No. | X | R₄ | R₅ | Mp (°C) |
|---|---|---|---|---|
| 25 | hydantoin-COOCH₃ | —OCH₃ | —SO₂—N(CH₃)(C₁₈H₃₇) | 154 |
| 26 | hydantoin-COO—C₄H₉(i) | OC₁₆H₃₃ | —SO₂—N(CH₃)(CH₃) | 109 – 111 |
| 27 | imidazolidinedione-CH₃, COOC₂H₅ (N-CH₂OC₂H₅O-) | OC₁₆H₃₃ | SO₂N(CH₃)(CH₃) | oily |
| 28 | imidazolidinedione-COOCH₃ (N-C₂H₅) | OC₁₆H₃₃ | SO₂NH—CH₃ | 122 – 124 |
| 29 | imidazolidinedione-COOC₄H₉ (N-C₂H₅) | OC₁₆H₃₃ | SO₂—NH—CH₃ | oily |
| 30 | imidazolidinedione-COOC₄H₉(i) (N-H) | Cl | —NH—CO—O—CH₂—CH₂—O—[phenyl-C₄H₉(t), cyclopentyl] | 182 – 183 |

Table 1-continued
| No. | X | R₄ | R₅ | Mp (°C) |
|---|---|---|---|---|
| 31 |  | OC₁₆H₃₃ |  | 132 – 134 |
| 32 |  | Cl | 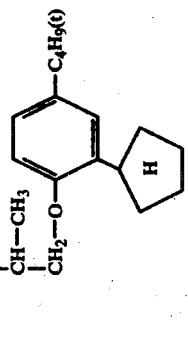 | 161 – 164 |
| 33 |  | Cl | 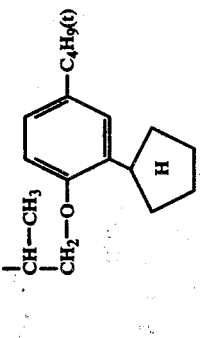 | 166 – 170 |
| 34 | 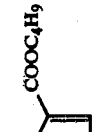 | Cl | 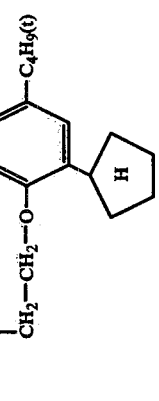 | 182 – 183 |

Table 1-continued

| No. | X | R4 | [structure] | Mp (°C) |
|---|---|---|---|---|
| 35 | [dichlorophenyl-ethyl-hydantoin structure] | OCH₃ | t-butyl—C(=O)—CH(X)—CONH—[phenyl(R4,R5)]—NH—CO—O—CH(CH₃)—CH₂—O—[phenyl with C₄H₉(t) and cyclopentyl(H)] | 118 – 120 |

| # | Structure | Mp. |
|---|---|---|
| 36 | | Mp. 70° C |
| 37 | | Mp. 86–88° C |
| 38 | | Mp. 84° C |
| 39 | | oily |
| 40 | | oily |
| 41 | | Mp. 94–97° C |
| 42 | | |
| 43 | | |

-continued
44 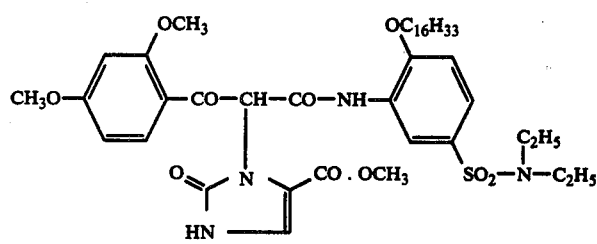
45 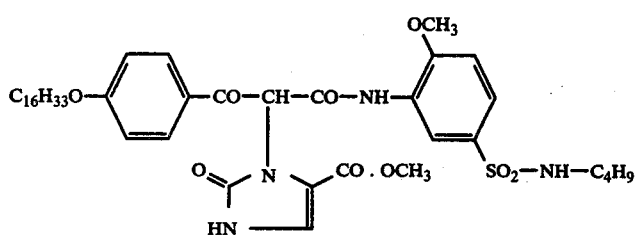
46 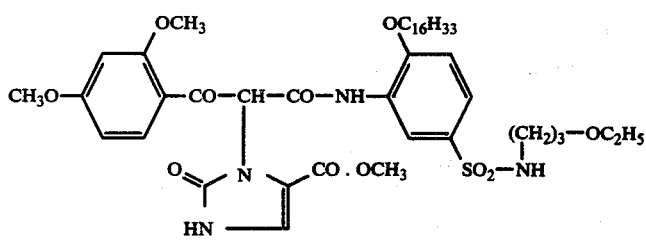
47 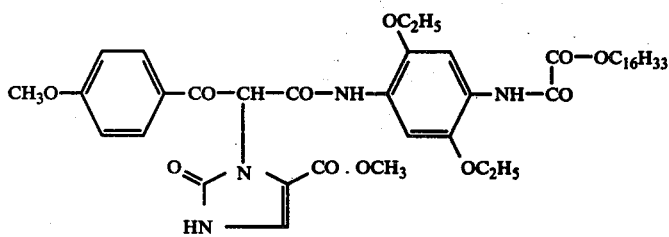
48 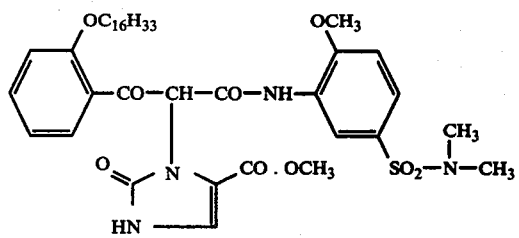
49 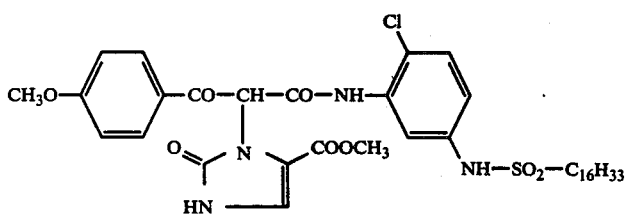
50 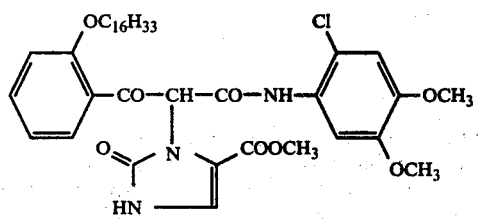

51

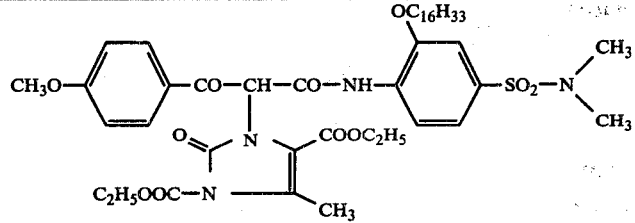

52

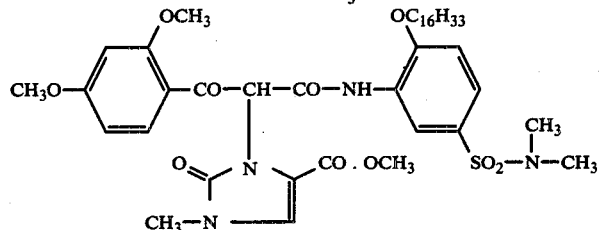

53

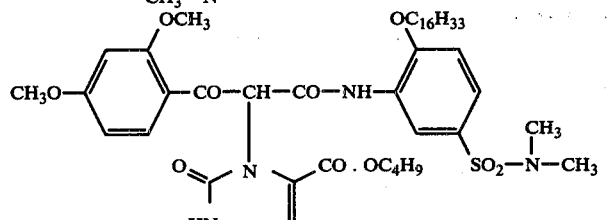

54

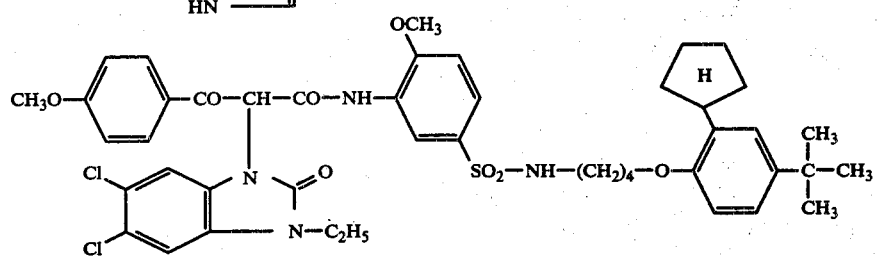

55

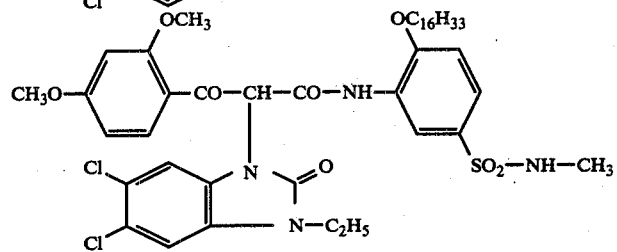

56

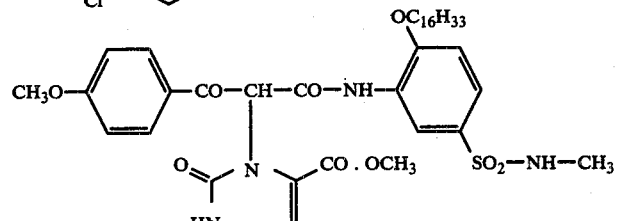

57

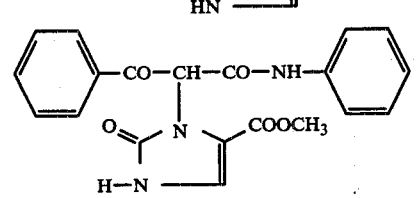

To prepare the 2-equivalent yellow-forming couplers according to the present invention, a 2-equivalent yellow-forming coupler containing chlorine as removable substituent in the activated methylene group is reacted with a suitable substituted 1,3-diazolone-2 in the presence of a base. Suitable 1,3-diazolones-2 are mainly imidazolinones having at least an alkoxycarbonyl substituent or benzimidazolinones-2 which contain two chlorine atoms in the condensed benzene ring. Imidazolinones-2 having in 4- and/or 5-position an alkoxycarbonyl group in which the alkoxy group contains 1 to 5 carbon atoms are preferred.

The reaction may be carried out in an aprotic solvent such as acetonitrile or dimethylformamide or an aliphatic amine, a basic heterocyclic compound or an alkali metal salt of an alcohol being used as the base. The reaction may advantageously be carried out at 20 to 100° C, preferably at 40 to 80° C, in the presence of hexamethylphosphoric acid triamide as solvent, the base used being preferably sodium methylene or potassium tertiary butylate, generally in equimolar amounts depending on the amount of 1,3-diazolone-2 used. Higher amounts of base up to 200% molar excess may be used.

The reaction of an imidazolinone carboxylic acid ester generally gives rise to the position isomers in varying proportions depending on the nature of the 2-equivalent coupler, the carboxylic acid ester group being situated in the 4- or 5-position of the heterocyclic splittable group. Substitution generally occurs on that nitrogen atom which is most easily capable of forming the corresponding anion by reaction with the base. In the case of ortho-alkoxy substituted benzoyl acetanilides, however, a considerable proportion of the stereoisomer is also formed which shows less steric hindrance and in which the substituent on the heterocyclic group is in the 4-position.

Preparation of the 1,3-diazolones-2, which may be substituted, may be carried out by known methods, for example 5,6-dichlorobenzimidazolone is prepared by the method described in Chem. Ber. 32, 2190. Imidazolinone-2-carboxylic acid is prepared by the reaction of tartaric acid with urea in the presence of sulfuric acid. The corresponding esters can be prepared from it in known manner by reaction with aliphatic alcohols.

Preparation of the couplers according to the invention is described in detail below:

Preparation of Coupler No. 8

1st Stage:

Imidazolinone-2-carboxylic acid: 300 g (2 mol) of tartaric acid are mixed vigorously with 240 g (4 mol) of urea and the mixture is introduced portionwise into 1000 ml of concentrated sulfuric acid with stirring at such a rate that the temperature does not rise above 65° C. Stirring of the reaction mixture is continued for 2 to 3 hours at 100° C and the mixture is then cooled to 5 to 10° C and stirred into 2.5 kg of ice. The reaction product is then suction filtered, washed with cold water until the washing liquid has a pH of 4.5 and then rewashed with acetone or methanol. The yield was 95 g, and the product had a melting point of 260° C.

2nd Stage:

Imidazolinone-2-carboxylic acid methyl ester: 50 g of the imidazolinone-2-carboxylic acid prepared in stage 1 are dissolved in 80 ml of concentrated sulfuric acid at 100 to 110° C, and 280 ml of methanol are then slowly added dropwise at about 80° C. The reaction mixture is then stirred for 3 hours at 100° C, cooled and stirred into 600 g of ice. The reaction product is suction filtered, carefully treated with dilute soda solution in the cold and washed until neutral. The yield was 40 g, and the product had a melting point of 290° C.

3rd Stage:

Preparation of Coupler No. 8

8.5 g (60 mMol) of imidazolinone-2-carboxylic acid methyl ester, 6.7 g (60 mMol) of potassium tertiary butylate and 70 ml of hexamethylphosphoric acid triamide are stirred in a flask. 26.4 g (45 mMol) of α-chloro-pivaloyl-(2-hexadecyloxy-5-N-methylsulfamoyl)-acetanilide are dissolved in 100 ml of hexamethylphosphoric acid triamide and slowly added dropwise to the above mixture at 40° C and stirred for one hour. The solution is then poured on approximately 500 ml of a mixture of ice water and hydrochloric acid, suction filtered and washed neutral with cold water. The residue is taken up in acetonitrile and suction filtered. It is then recrystallized from acetonitrile and alcohol. The yield was 14 g, and the product had a melting point of 96 – 98° C.

Preparation of Coupler No. 9

1st Stage:

Imidazolinone-2-carboxylic acid isobutyl ester: 47 g of imidazolinone-2-carboxylic acid (prepared as described in the preparation of Coupler No. 8) and 240 ml of isobutanol are stirred in a flask and 50 ml of concentrated sulfuric acid are slowly added dropwise. When all the sulfuric acid has been added, the mixture is boiled under reflux until a clear solution is obtained (approximately 3 – 5 hours). The solution is then poured on a mixture of ice and hydrochloric acid, the precipitate is suction filtered and the residue is stirred up with dilute soda solution in the cold, filtered and washed with cold water and then with acetone. The yield was 17 g, and the product had a melting point of 242° C.

2nd Stage:

13.3 g of imidazolinone-2-carboxylic acid isobutyl ester are stirred up with 8.8 g of potassium tertiary butylate in 70 ml of hexamethylphosphoric acid triamide. 34 g of α-chloro-α-pivaloyl-(2-hexadecyloxy-5-N-methylsulfamoyl)-acetanilide are dissolved in 120 ml of hexamethylphosphoric acid triamide and the solution is added dropwise to the above described mixture at 35 to 40° C and then stirred for 1 to 1 ½ hours at 35 to 45° C. The reaction mixture is then poured on a mixture of ice water and hydrochloric acid, suction filtered and washed. The residue is stirred up in methanol, suction filtered and recrystallized first from acetonitrile and then from methanol. The yield was 16.5 g, and the product had a melting point of 101 to 103° C.

Preparation of Coupler No. 39

The preparation of imidazolinone-2-carboxylic acid-isobutylester is carried out as described in the preparation of Coupler No. 9.

9.6 g (52 mMol) of imidazolinone-2-carboxylic acid isobutylester, 5.8 g (52 mMol) of potassium tertiary butylate and 50 ml of hexamethylphosphoric acid triamide are stirred in a flask. 14 g (26 mMol) of α-chloro-(2'-hexadecyloxy)-benzoyl-2-methoxy-acetanilide are dissolved in 70 ml of hexamethylphosphoric acid triamide and the solution is added dropwise at 50° C to the mixture previously described. The mixture is then stirred for 4 hours at 50° C and poured on a mixture of ice water and hydrochloric acid. The residue is purified by column chromatographic purification.

The yield was 6 g of Coupler No. 39, and the product was oily.

Preparation of Coupler No. 14

0.1 mol of α-chloro-α-pivaloyl-(2-hexadecyloxy-5-N-methyl-sulfamoyl)-acetanilide are dissolved in 50 ml of hexamethylphosphoric acid triamide. 0.2 mol of 5,6-dichloro-N-ethyl-benzimidazolone-2 (prepared by the method given in Chem. Ber. 32, 2190) and 0.2 mol of sodium methylate are added at room temperature and stirred for 2 hours. The reaction mixture is then poured on a mixture of ice water and hydrochloric acid and filtered and the reaction product is dissolved in ethyl acetate.

After redrying of the ethyl ester solution with calcium chloride, the residue is concentrated by evaporation and the precipitated crystals are recrystallized from methanol. The yield was 74%, and the product had a melting point of 80° C.

Preparation of coupler No. 5

First stage:
172.5 g of 2-chloro-5-nitraniline were dissolved in 863 ml of xylene, and water was removed by distilling of about 300 ml of a mixture of xylene and water. 225 g of methyl pivaloyl acetate (about 30% excess) were added within 4 hours and the removal of a mixture of xylene and volatiles was continued by distillation. After 4 hours additional 40 g of methyl pivaloyl acetate are added and the heating was continued for 2 hours. Most of the solvent was then removed under reduced pressure and the residue was mixed with 500 ml of methanol and kept over night in a refrigerator. The resulting crystals were washed with 100 ml of cold methanol. The yield was 174 g and the melting point was 119° C.

Second stage:
164 g of the product obtained in the first stage were dissolved at 60° C in 920 ml of acetic acid and a mixture of 49.5 ml of sulfuryl chloride and 127 ml of acetic acid were added within 30 minutes. The reaction product was suction-filtered and washed with acetic acid and petroleum ether. The yield was 150 g and the melting point was 155° C.

Third stage:
105 g of imidazlinone-2-carboxylic acid methyl ester (0.6 mol excess) were dissolved by heating in 1,400 ml of dimethyl acetamide. The mixture was cooled and at 80° C 150 ml of tetramethyl guanidine were added and 150 g of the product obtained in the second stage were added within 30 minutes to the mixture. Stirring was continued at 40° C for 2 hours and then over night at room temperature. The solution was then poured on a mixture of ice-water and hydrochloric acid suction-filtered and washed with water. The product was then again suspended in water suction-filtered, dried and recrystallized from aceto-nitrile. The yield was 138 g and the melting point was 154–157° C.

Fourth stage:
138 g of the product obtained in the third stage (α-pivaloyl-α-(5-methoxycarbonyl-1-imidazolinonyl)-2-chloro-5-nitroacetanilide) were dissolved in a mixture of 1200 ml of ethanol and 300 ml of dimethylformamide and catalytically hydrogenated at 30° C under a hydrogen pressure of 10 atmospheres gauge. The reaction solution was heated to boiling and suction-filtered. The solvent was removed under reduced pressure. The residue was suspended in acetonitrile suction-filtered and washed with acetonitrile. The yield was 120 g and the melting-point was 225 – 230° C.

Fifth stage:
19.5 g of 4-chloro-2-tetradecylphenoxy-acetylchloride were added during 30 minutes at 30–40° C to a solution of 15.3 g of the product obtained in stage 4 in 100 ml of pyridine. The reaction mixture was poured on to a mixture of ice-water and hydrochloric acid and taken up in ethylacetate, washed, dried and concentrated. The residue was purified by chromatography over silica gel using a mixture of 2 parts ethyl acetate and 1 part of chloroform. After concentration the product was dissolved in petroleum ether and precipitated with ether, filtered, dried and centrifuged.

Preparation of coupler No. 17

15 g of

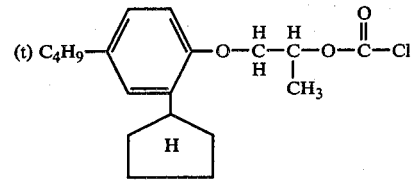

were added to a solution of 14 g of the product obtained in stage 4 in preparation of coupler 5 in 100 ml of pyridine at 30–40° C during 30 minutes. The reaction composition was poured in a mixture of ice and hydrochloric acid, taken up in ethyl acetate, washed, dried and concentrated. The residue was purified over silica gel using a mixture of 2 parts of ethyl acetate and 1 part of chloroform as solvent. After concentration the product was dissolved in a small amount of ethylether, filtered, precipitated with petroleum ether, suction-filtered and washed with petroleum ether. The melting point was 136–144° C.

Preparation of the other couplers may be carried out in a similar manner.

The yellow-forming couplers need not necessarily be incorporated in the light-sensitive layers but may be accomodated in a layer of binder adjacent to the light-sensitive silver halide emulsion layer.

Depending on the kind of the yellow-forming coupler group A used according to the definitions given above, the yellow-forming couplers according to the invention may be used either as diffusion-fast couplers or as non-diffusionfast couplers to form yellow color images in photographic materials. To obtain sufficiently high diffusionfastness, the yellow coupler group A contains groups which confer diffusion-fastness, e.g. straight or branched chain alkyl groups containing 10 to 18 carbon atoms, or they may be substituted with alkyl substituted phenoxy groups which may be attached to the coupler group A optionally via an aromatic group either directly or indirectly, for example through —O—, —S—, —CONH—, —NHCO—, —SO$_2$NH—, —NHSO$_2$— or other intermediate links.

When preparing the light-sensitive color material according to the invention, the diffusion resistant yellow-forming couplers according to the above general formulae may be incorporated by any known technique in the casting composition of the silver halide emulsion layers or of other colloid layers which are in water-permeable relation thereto. For example, the water-soluble color couplers, i.e. those which contain one or more water-solubilizing groups such as a sulfo or carboxyl group (in acid or salt form), may be incorporated in the casting composition of the layer in question by applying them from an aqueous solution while those color couplers which are insoluble or insufficiently soluble in water may be applied from a solution in suitable water-miscible or immiscible high boiling or low boiling organic solvents or mixtures thereof. The resulting solution is then dispersed in a hydrophilic colloid composition, optionally in the presence of a wetting or dispersing agent this colloid composition constituting either all or only part of the binder of the colloid layer. The hydrophilic colloid composition may, of course, contain any other ingredients in addition to the colloid. The water-insoluble color couplers which contain fluorosulfonyl groups or carboxylic acid ester groups such as ethoxycarbonyl groups may also be converted by alkaline hydrolysis into the corresponding sulfonic acids or carboxylic acids which can be incorporated successively in hydrophilic colloid compositions by applying them in the form of aqueous solutions of their alkali metal salts.

The solution of color coupler need not be directly dispersed or dissolved in the casting composition of the silver halide emulsion or some other water-permeable layer. The solution may advantageously first be dispersed or dissolved in an aqueous light-insensitive solution of a hydrophilic colloid, whereupon the resulting mixture, optionally after removal of the organic solvent used, is intimately mixed with the casting composition of the light-sensitive silver halide emulsion layer or other water-permeable layer just before casting. Further details about particularly suitable techniques for incorporating color couplers in hydrophilic colloid layers of a photographic material may be found in published Dutch Pat. No. 65.16423, 65.16424, 66.00098, 66.00099 and 66.00628; Belgian Pat. No. 750.889; U.S. Pat. No. 2,304,940 and British Patent Specification No. 791,219.

To prepare photographic color images according to the invention, an exposed silver halide emulsion layer is developed with an aromatic primary amino developer substance in the presence of a color coupler according to the invention. The developer substance used may be any color developer substances which are capable of yielding azomethine dyes. Suitable developer substances include aromatic compounds such as p-phenylenediamine and its derivatives, for example N,N-dialkyl-p-phenylenediamine such as N,N-diethyl-p-phenylenediamine, N,N-dialkyl-N'-sulfomethyl-p-phenylenediamine and N,N-dialkyl-N'-carboxymethyl-p-phenylenediamine.

Suitable light-sensitive emulsions are emulsions of silver halides such as silver chloride, silver bromide or mixtures thereof, which may have a small silver iodide content of up to 10 mols-%, used in one of the conventional hydrophilic binders. The binder used for the photographic layers is preferably gelatin, although this may be partly or completely replaced by other natural or synthetic binders. Suitable natural binders are e.g. alginic acid and its derivatives such as its salts, esters or amides, cellulose derivatives such as carboxymethylcellulose, alkylcellulose such as hydroxyethylcellulose, starch or its derivatives such as ethers or esters or carrageenates. The synthetic binders include polyvinyl alcohol, partly saponified polyvinyl acetate and polyvinyl-pyrrolidone.

The emulsions may also be chemically sensitized, e.g. by adding sulfur compounds such as allylisothiocyanate, allylthiourea and sodium thiosulfate at the stage of chemical ripening. Reducing agents may also be used as chemical sensitizers, e.g. the tin compound described in Belgian Pat. No. 493,464 and 568,687, or polyamines such as diethylene triamine or aminoethane sulfinic acid derivatives, e.g. according to Belgian Pat. No. 547,323.

Noble metals such as gold, platinum, palladium, iridium, ruthenium or rhodium and compounds of these metals are also suitable chemical sensitizers. This method of chemical sensitization has been described in the article by R. KOSLOWSKY, Z. Wiss. Phot. 46 (1951) 65 - 72.

The emulsions may also be sensitized with polyalkylene oxide derivatives, e.g. with a polyethylene oxide which has a molecular weight of between 1,000 and 20,000 or with condensation products of alkylene oxide and aliphatic alcohols, glycols, cyclic dehydration products of hexitols, with alkyl-substituted phenols, aliphatic carboxylic acids, aliphatic amines, aliphatic diamines and amides. The condensation products have a molecular weight of at least 700, preferably more than 1000. These sensitizers may, of course, be combined in order to achieve special effects as described in Belgian Pat. No 537,278 and British Pat. Specification No. 727,982.

The emulsions must have sufficient sensitivity in the blue spectral region. Non-sensitized emulsions whose sensitivity is due to the intrinsic sensitivity of the silver halides are generally used for this purpose although the silver halide emulsions may be spectrally sensitized in the blue region, e.g. by means of sensitizers of the kind described in British Patent Specification No. 1,285,078.

The emulsions may contain the usual stabilizers, e.g. homopolar or salt-type compounds of mercury which contain aromatic or heterocyclic rings such as mercaptotriazoles, simple mercury salts, sulfonium mercury double salts and other mercury compounds. Azaindenes are also suitable stabilizers, particularly tetra- or penta-azaindenes and especially those which are substituted with hydroxyl or amino groups. Compounds of this kind have been described in the article by BIRR, Z. Wiss. Phot. 47 (1952) 2 - 27. Other suitable stabilizers include heterocyclic mercapto compounds, e.g. phenyl-mercaptotetrazole, quaternary benzothiazole derivatives and benzotriazole.

The emulsions may be hardened in the usual manner, for example with formaldehyde or halogenated aldehyde, which contain a carboxyl group, such as mucobromic acid, diketones, methanesulfonic acid esters and dialdehydes.

The advantageous properties of the couplers according to the invention will be described below with the aid of some examples.

EXAMPLE 1

2 mMol of Coupler 8 are dissolved in 3 ml of ethyl acetate and then emulsified in 20 ml of a 5% gelatin solution in known manner at 60° C after the addition of 1 g of dibutyl phthalate and 0.16 g of the sodium salt of dodecylbenzene sulfonic acid.

The emulsion is then mixed with 85 g of a 7.5% gelatin solution which contains 1.93 g of silver bromide in a dispersed form, and is then diluted with water until it has a suitable viscosity for casting.

After the resulting emulsion has been cast on a transparent cellulose triacetate substrate, the photographic material produced in this way is exposed behind a grey step wedge and cut up into several samples. Some of the samples are directly developed for 5 minutes in a conventional color developer containing N,N-diethyl-p-phenylenediamine as developer substance and bleached and fixed in the usual manner.

Other samples are stored in a heating cupboard at 57° C and 34% relative humidity for 7 days before they are processed. A comparison of the two sets of samples is shown in Table 2 below, in which the criteria used for assessing the results are the basic fog S, the increase in basic fog ΔS, the increase in sensitivity ΔE as compared with a coupler of U.S. Pat. No. 3,265,506, and the color density loss of samples which have been subjected to storage before they were processed, compared with the results obtained from the immediately processed samples, the results being given in relative values.

Additional color wedges were prepared in a similar manner except that instead of 2 mMol of Coupler No. 8, 2 mMol of a coupler of the following formula were used:

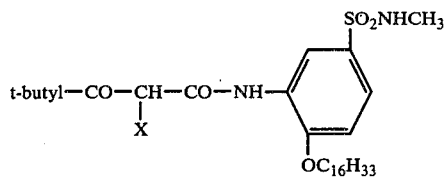

wherein X has the meaning shown in Table 2 below. Table 2 also compares a similar coupler from German Offenlegungsschrift No. 2,329,587 and the 4-equivalent yellow-coupler according to U.S. Pat. No. 3,265,506.

Table 2 t-butyl—CO—CH—CO—NH—[phenyl with $SO_2NHCH_3$ and $OC_{16}H_{33}$]
         |
         X

| Coupler No. | X | ΔS | S | ΔE(DIN) | loss in density (%) |
|---|---|---|---|---|---|
| 8 | O=⟨N⟩–COOCH₃ (HN) | 0.03 | 0.09 | + 1 | 0 |
| 9 | O=⟨N⟩–COOC₂H₉(iso) (HN) | 0.03 | 0.09 | + 2 | 0 |
| 14 | O=⟨N⟩–(dichlorophenyl) (C₂H₅N) | 0.05 | 0.09 | + 2 | 0 |
| for comparison DOS 23 29 587 | N–COOCH₃ / N–COOCH₃ | 0.15 | 0.12 | ± 0 | − 3 % |
| according to US-P 3,265,506 | Cl | 0.05 | 0.16 | + 5 | − 25 % |
| according to US-P 3,265 506 | H | 0.02 | 0.09 | ± 0 | 0 |

A comparison of the results shows that the yellow-forming couplers according to the invention are equal to the 4-equivalent yellow couplers known in the art in their low tendency to produce a photographic basic fog and almost equal in stability when stored under moist, warm conditions, as expressed by the S and color density loss values, but that they have a higher reactivity, as expressed by the increase in DIN values. Moreover, the reactivity of the yellow-forming couplers according to the invention is superior to that of the comparison couplers other than the undesirable coupler containing the splittable chlorine.

We claim:
1. A 2-equivalent yellow-forming coupler having the formula

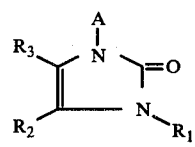

in which
$R_1$ represents hydrogen; an alkyl group containing 1 to 4 carbon atoms; or an alkoxy carbonyl group in which the alkoxy group contains from 1 to 5 carbon atoms;

$R_2$ and $R_3$ represent either the same or different substituents selected from the group consisting of hydrogen, alkyl, and alkoxycarbonyl in which the alkoxy group contains from 1 to 5 carbon atoms, but at least one of $R_2$ and $R_3$ represents an alkoxy carbonyl group; or $R_2$ and $R_3$ together represent the atoms required to complete a condensed benzene ring, which ring is further substituted with two chlorine atoms to form the 5, 6-dichlorobenzimidazolone group; and A represents a radical of a yellow-forming coupler having an open-chain keto-methylene structure in which the methylene group is activated by two attached carbonyl groups or by one carbonyl and one cyano group, and the radical being obtained by removing a hydrogen atom from the activated methylene group of a 4-equivalent yellow-forming coupler.

2. A coupler as claimed in claim 1 in which the $R_2$ and/or $R_3$ substituent is a methoxy-carbonyl group.

3. A coupler as claimed in claim 1 in which the $R_2$ and/or $R_3$ substituent is a butoxy-carbonyl group.

4. A coupler as claimed in claim 1 in which the yellow-forming coupler is a pivaloyl acetanilide or benzoylacetanilide.

5. A coupler as claimed in claim 1 in which the formula is that of the 3-ethyl-5,6-dichlorobenzimidazolone group.